United States Patent
Craft et al.

(10) Patent No.: US 9,459,187 B2
(45) Date of Patent: Oct. 4, 2016

(54) BLOOD COLLECTION DEVICE CONTAINING LYSOPHOSPHOLIPASE INHIBITOR

(75) Inventors: David Craft, Sparta, NJ (US); Priyanka Apte, Cedar Knolls, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/003,033

(22) PCT Filed: Mar. 2, 2012

(86) PCT No.: PCT/US2012/027391
§ 371 (c)(1),
(2), (4) Date: Oct. 16, 2013

(87) PCT Pub. No.: WO2012/121998
PCT Pub. Date: Sep. 13, 2012

(65) Prior Publication Data
US 2014/0030754 A1   Jan. 30, 2014

Related U.S. Application Data

(60) Provisional application No. 61/449,337, filed on Mar. 4, 2011.

(51) Int. Cl.
| C12Q 1/00 | (2006.01) |
| G01N 1/28 | (2006.01) |
| A61B 5/15 | (2006.01) |
| A61B 5/154 | (2006.01) |

(52) U.S. Cl.
CPC .............. *G01N 1/28* (2013.01); *A61B 5/1438* (2013.01); *A61B 5/15003* (2013.01); *A61B 5/154* (2013.01); *A61B 5/150099* (2013.01); *A61B 5/150351* (2013.01); *A61B 5/150755* (2013.01)

(58) Field of Classification Search
None
See application file for complete search history.

(56) References Cited

U.S. PATENT DOCUMENTS

| 7,309,468 | B2 | 12/2007 | Stevens et al. | |
| 2005/0124965 | A1* | 6/2005 | Haywood | 604/500 |
| 2005/0148549 | A1 | 7/2005 | Dennis et al. | |
| 2007/0134753 | A1 | 6/2007 | Barbier et al. | |
| 2014/0030754 | A1 | 1/2014 | Craft et al. | |

FOREIGN PATENT DOCUMENTS

| CN | 1354799 A | 6/2002 |
| CN | 1564828 A | 1/2005 |
| CN | 101294187 A | 10/2008 |
| CN | 203203992 U | 9/2013 |
| EP | 1113269 A2 | 7/2001 |

(Continued)

OTHER PUBLICATIONS

BD P800 Brochure (2009).*

(Continued)

*Primary Examiner* — Thomas J Visone
(74) *Attorney, Agent, or Firm* — Lerner, David, Littenberg, Krumholz & Mentlik, LLP (57) ABSTRACT

Disclosed are collection devices for collecting and stabilizing whole blood or a component thereof, which include a first end and a second end and at least one interior wall defining a reservoir, wherein the reservoir contains a stabilization agent that includes a lysophospholipase (LysoPLA) inhibitor. Also disclosed are methods for making and using the devices.

35 Claims, 3 Drawing Sheets

STABILITY OF Ghrelin OVER TIME (with 1mM MAFP AT 25 deg)

(56) References Cited

FOREIGN PATENT DOCUMENTS

| EP | 2302384 | A1 | 3/2011 |
|---|---|---|---|
| JP | H10507770 | A | 7/1998 |
| JP | 2005519134 | A | 6/2005 |
| JP | 2006524482 | A | 11/2006 |
| WO | 9613158 | A2 | 5/1996 |
| WO | 03040309 | A2 | 5/2003 |
| WO | 2008147245 | A2 | 12/2008 |
| WO | 2009042922 | A2 | 4/2009 |
| WO | 2010008315 | A1 | 1/2010 |

OTHER PUBLICATIONS

Ahmed et al., Chem, Bio. Inter., 162:165-171 (2006).*
International Search Report and Written Opinion for Application No. PCT/US2012/027391 dated Jul. 10, 2012.
M. Satou et al: "Identification and Characterization of Acyl-Protein Thioesterase 1/Lysophospholipase I as a Ghrelin Deacylation/Lysophospholipid Hydrolyzing Enzyme in Fetal Bovine Serum and Conditioned Medium", Endocrinology, vol. 151, No. 10, Oct. 1, 2010, pp. 4765-4775, XP55031522.
Shanado Y et al: "Lysophospholipase I identified as a ghrelin deacylation enzyme in rat stomach", Biochemical and Biophysical Research Communications, Academic Press Inc. Orlando, FL, US, vol. 325, No. 4, Dec. 24, 2004, pp. 1487-1494, XP004649774.
Spedding M et al,"Direct Activation of Calcium Channels by Palmitoyl Carnitine a Putative Endogenous Ligand", British Journal of Pharmacology, vol. 92, No. 2, 1987, pp. 457-468, XP008153220, ISSN: 0007-1188.
Qi Gu et al, "Simultaneous determination of enalapril and enalaprilat in human plasma by liquid chromatography-tandem mass spectrometry", Journal of Chromatography B, vol. 813, pp. 337-342, Dec. 31, 2004.
Tokumura et al, "Identification of human plasma lysophospholipase D, a lysophosphatidic acid-producing enzyme, as autotoxin, a multifunctional phosphodiesterase", Journal of Biological Chemistry, vol. 277, pp. 39436-39422, Aug. 9, 2002.
Wikipedia vacutainers [retrieved from internet Jul. 13, 2016] URL: http://web.archive.org/web/20100523101159/http://en.wikipedia.org/wiki/Vacutainer published on May 23, 2010 as per Wayback machine, pp. 1-2.

* cited by examiner

FIG.1

BLOOD COLLECTION DEVICE CONTAINING LYSOPHOSPHOLIPASE INHIBITOR

CROSS-REFERENCE TO RELATED APPLICATIONS

This application claims the benefit of the filing date of U.S. Provisional Patent Application No. 61/449,337 filed Mar. 4, 2011, the disclosure of which is hereby incorporated herein by reference.

BACKGROUND OF THE INVENTION

Diabetes is a syndrome of disordered metabolism, usually due to a combination of hereditary and environmental causes, resulting in abnormally high blood sugar levels (hyperglycemia). Blood glucose levels are controlled by a complex interaction of multiple chemicals and hormones in the body, including the hormone insulin made in the beta cells of the pancreas. Diabetes mellitus refers to the group of diseases that leads to high blood glucose levels due to defects in either insulin secretion or insulin action in the body.

Diabetes develops due to a diminished production of insulin (in type 1) or resistance to its effects (in type 2 and gestational). Both lead to hyperglycemia, which largely causes the acute signs of diabetes, namely excessive urine production, resulting compensatory thirst and increased fluid intake, blurred vision, unexplained weight loss, lethargy, and changes in energy metabolism.

The injections by a syringe, insulin pump, or insulin pen deliver insulin, which is a basic treatment of type 1 diabetes. Type 2 diabetes is managed with a combination of dietary treatment, exercise, medications and insulin supplementation. All forms of diabetes have become treatable since insulin became medically available, but there is still no cure.

According to a World Health Organization report in 2000, at least 171 million people worldwide were suffering from diabetes, or 2.8% of the population. Its incidence is increasing rapidly, however, and it is estimated that by the year 2030, this number will almost double. Diabetes mellitus occurs throughout the world, but is more common (especially type 2) in the more developed countries. The greatest increase in prevalence is, however, expected to occur in Asia and Africa, where most patients will likely be found by 2030.

Glucagon-like peptide (GLP-1), gastric inhibitory peptide (GIP), glucagon and ghrelin have been reported as peptide biomarkers of metabolic diseases such as diabetes. The major source of GLP-1 in the body is found in the intestines. The typical normal blood concentration of GLP-1 in circulation is in a range of 3-85 picomolar. GLP-1 possesses several physiological properties that make it a subject of intensive investigation as a potential treatment of diabetes. Gautier, et al., Diabetes Met. 31:233-42 (2005). GLP-1 is known to increase insulin secretion from the pancreas, decrease glucagon secretion from the pancreas, increase beta cell mass and insulin gene expression, inhibit acid secretion and gastric emptying in the stomach, and decrease food intake by increasing satiety. Baggio, et al., J. Gastroenterol. 132:2131-57 (2007). Once in circulation, however, GLP-1 has been reported to exhibit a short biological half-life of about 1.5-5 minutes (Hui, et al., Eur. J. Endocrinol. 146: 863-9 (2002)), due to proteolytic degradation caused by the proteases including dipeptidyl peptidase (DPP)-IV.

The active form of GIP is a 42-amino acid polypeptide represented by the sequence: YAEGTFISDYSIAMDKI-HQQDFVNWLLAQKGKKNDKHNITGQ ("$GIP_{(1-42)}$"). $GIP_{(1-42)}$ is synthesized by K cells which are found in the mucosa of the duodenum and the jejunum of the gastrointestinal tract. It is believed that $GIP_{(1-42)}$ induces insulin secretion via a mechanism that involves interaction between GIP and 7 transmembrane $GIP_{(1-42)}$ receptors on pancreatic beta-cells. The normal fasting concentration of $GIP_{(1-42)}$ in plasma is about 6-12 pmol/L, whereas the normal non-fasting concentration is about 80-300 pmol/L. $GIP_{(1-42)}$ has been reported to exhibit a half-life in circulation of about 5 minutes.

Glucagon, a 29-amino acid peptide, is involved in carbohydrate metabolism. Produced by the pancreas, it is released when the glucose level in the blood is low (hypoglycemia). It binds to receptors on liver cells (hepatocytes), causing the liver to convert stored glycogen into glucose and release then release the glucose into the bloodstream. As these stores become depleted, glucagon then stimulates synthesis of additional glucose in the liver. The action of glucagon is thus opposite that of insulin, which instructs the cells in the body to take in glucose from the blood. Glucagon also regulates the rate of glucose production through a process known as lipolysis. Typical normal blood concentration of glucagon in circulation is 11-17 picomolar. Once in circulation, glucagon has a half-life of about 8-18 minutes.

Ghrelin is a hormone produced mainly by P/D1 cells lining the fundus of the human stomach and epsilon cells of the pancreas that stimulates appetite. Typical normal blood concentration is also in the picomolar range. Ghrelin is a 28-amino acid peptide having the sequence $NH_2$-GSSFL-SPEHQRVQQRKESKKPPAKLQPR-COOH. One of the biologically active forms of this peptide, known as acylated ghrelin, contains an n-octanoyl group on Ser3 (i.e., —$CH_3$($CH_2)_6$COO—). This peptide exerts endocrine actions such as stimulation of Growth Hormone (GH) release from the pituitary gland, and various physiological effects such as induction of adiposity (increase in fat tissue) and body weight gain due to appetite-stimulating effects and increased food intake, and stimulation of gastric acid secretion and motility. Kojima, et al., Trends Endocrinol. Metab. 12:118-122 (2001); Kojima, et al., Physiol. Rev. 85:495-532 (2005). Thus, in addition to diabetes, acylated ghrelin is a known metabolic biomarker for related conditions such as diet-induced weight loss and fasting. Another form of ghrelin peptide is known as des-acyl-ghrelin, which is a metabolically inactive form having its own functions including the modulation of cell proliferation (Baldanzi, et al., J. Cell Biol. 159:1029-37 (2002); Ariyasu, et al., Endocrinol. 2005:355-64 (2005)) and adipogenesis (Muccioli, et al., Eur. J. Pharmacol. 498:27-35 (2004)). Normal plasma concentration of ghrelin, including both active and inactive forms, ranges from about 300 to about 700 pg/ml (or about 0.08 to about 0.19 nM or about 0.09 to about 0.19 fmol/µl), and fluctuates with time. The major circulating form of ghrelin is dec-acyl ghrelin [Hosoda, et al., Biochim. Biophys. Res. Comm. 279:909-13 (2000)], and thus the majority of this amount is not in the form of the more accurate metabolic biomarker. Once in circulation, ghrelin has a half-life of about 30 minutes.

Yi, et al., J. Proteome Res. 6(5):1768-81 (2007), for example, reports that proteolytic degradation of serum and plasma proteins caused by intrinsic proteases occurs during the first minutes of sample collection and handling (which suggests rapid ex vivo proteolytic degradation). In a subsequent publication, Yi et al., J. Proteome Res. 7(12):5112-8

(2008), reports that although the discovery of disease markers in blood fluid continues to accelerate as proteomics technology becomes both more powerful and more widely available, there has been notably less success in transitioning these discoveries into clinical utility, spurring a growing interest in understanding the barriers to this transition. Aside from the short half-lives and the rather small concentrations of GLP-1, GIP, glucagon and ghrelin (and particularly the biologically active forms thereof) in plasma, complications arise due to pre-analytical variability especially during blood collection and early sample handling. Yi (2008) also reports that in the case of some peptide biomarkers, proteolytic degradation occurs in a matter of seconds.

SUMMARY OF THE INVENTION

Ghrelin contains a peptide backbone and a side chain containing an 8-carbon ester group, which are susceptible to endogenous proteases and esterases respectively, that are present in human plasma. As shown in the working examples, Applicants have discovered that ghrelin can be more effectively stabilized in collected blood or fluid component (e.g., serum or plasma) samples by inclusion of a lysophospholipase (LysoPLA) inhibitor, as opposed to an inhibitor of a protease or an esterase. In fact, Applicants' data show that the additional presence of an esterase inhibitor detracted from or diminished stability of ghrelin in vitro. Aside from the fact that the side chain of ghrelin is an "ester" group, these discoveries are surprising and unexpected, especially in view of reports that LysoPLA activity is detected in the stomach and intestine, but not in plasma. Thus, the present invention affords relatively longer storage stability of blood or a component thereof for purposes of conducting reliable clinical testing such as measurement of biomarkers such as ghrelin.

Accordingly, a first aspect of the present invention is directed to a collection device for collecting and stabilizing whole blood or a component thereof, which includes a first end and a second end and at least one interior wall defining a reservoir, wherein the reservoir contains a stabilization agent that includes a lysophospholipase (LysoPLA) inhibitor. In some embodiments, the stabilization agent also includes at least one inhibitor of another type of enzyme that is normally present in blood and that degrades diagnostic markers of metabolic diseases. These enzymes include esterases and proteases. Thus, in other embodiments, the blood collection device may also include an inhibitor of an esterase, such as a butylcholinesterase (BChE) or an acetylcholinesterase (AChE) inhibitor, and/or an inhibitor of a protease (e.g., an inhibitor of a serine protease, an inhibitor of an exopeptidase, an inhibitor of a dipeptidyl peptidase, and combinations of two or more thereof).

Methods of making and using the devices for the purposes of collecting and storing whole blood or component(s) thereof are also provided.

A further aspect of the present invention is directed to a method for diagnosing a disease or monitoring treatment of an individual with a disease such as a metabolic disease (e.g., diabetes), comprising measuring over time (or at least one predetermined time or time interval) the presence or amount of one or more markers for the disease, including biologically (metabolically) active ghrelin, in a blood sample or component thereof collected from the patient using an inventive blood collection device. In some embodiments, the method also includes measuring at least one additional metabolic disease marker selected from glucagon, GIP, ghrelin and GLP-1 (which includes GLP-1-(7-36)NH$_2$ and GLP-1-(7-37)), and combinations of two or more thereof.

Yet a further aspect of the present invention is directed to a method for monitoring blood levels of a prodrug containing an aliphatic ester side group (e.g., acyl group) in an individual who has been administered the prodrug, which includes collecting a blood sample from the patient using the inventive blood collection device, and measuring the presence or amount of the prodrug and/or an active metabolite thereof, in the sample or a component thereof. The presence or amount of the prodrug and an active metabolite of the prodrug may be measured. The measurement of the blood levels of the prodrug and/or metabolite may be conducted more than once such as at predetermined time intervals.

DETAILED DESCRIPTION OF THE INVENTION

The collection devices of the present invention are used to collect and stabilize whole blood or a component thereof, such as red blood cell concentrates, platelet concentrates, leukocyte concentrates, and fluid components of blood including plasma and serum.

Broadly, the blood sample collection devices of the present invention can encompass any collection device including tubes such as test tubes and centrifuge tubes; closed system blood collection devices, such as collection bags; syringes, especially pre-filled syringes; catheters; microtiter and other multi-well plates; arrays; tubing; laboratory vessels such as flasks, spinner flasks, roller bottles, vials, microscope slides, microscope slide assemblies, coverslips, films and porous substrates and assemblies; pipettes and pipette tips; tissue and other biological sample collection containers; and any other container suitable for holding a biological sample, as well as containers and elements involved in transferring samples. Examples and illustrations of several such devices are disclosed in commonly owned U.S. Pat. No. 7,309,468 to Stevens et al.

Figure 1:
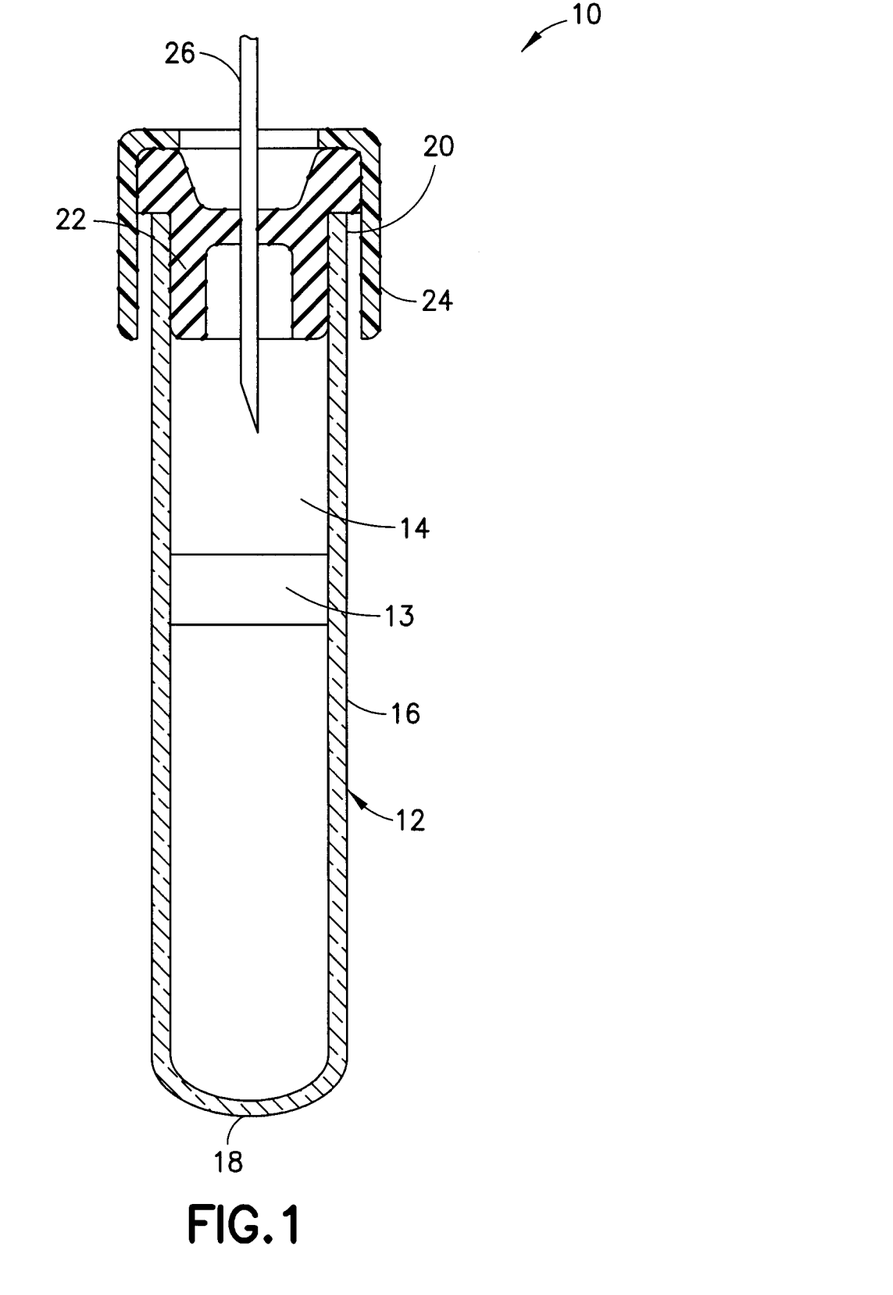
FIG. 1 is a perspective view of a typical blood collection device of the present invention.

FIG. 1, which is also illustrated in U.S. Pat. No. 7,309,468, shows a typical blood collection device 10, useful in the present invention, which includes a container 12 defining an internal chamber or reservoir 14. In the embodiment illustrated, container 12 is a hollow tube having a side wall 16, a closed bottom end 18 and an open top end 20. Optionally, a separating member 13 is provided within the container chamber 14. Separating member 13 serves to assist in separating components of the blood sample, for example, by centrifugation. Container 12 is dimensioned for collecting a suitable volume of blood. A closure means 22 for covering open end 20 to close container 12 is necessary where a sterile product is demanded. In some embodiments, the tube is configured for a screw cap. In embodiments wherein the tube is evacuated, however, as in the case where the reservoir contains a BChE inhibitor but not a protease inhibitor, a tight-fitting, elastomeric plug is generally employed to contain the vacuum during the required storage periods. Preferably, closure 22 forms a seal capable of effectively closing container 12 and retaining a biological sample in chamber 14. Closure 22 may be one of a variety of forms including, but not limited to, rubber closures, HEMOGUARD™ closures, metallic seals, metal-banded rubber seals and seals of different polymers and designs. A protective shield 24 may overlie closure 22.

Container 12 can be made of any material suitable for laboratory vessels, including, for example plastics (e.g., polyolefins, polyamides, polyesters, silicones, polyurethanes, epoxies, acrylics, polyacrylates, polyesters, polysulfones, polymethacrylates, PEEK, polyimide and fluoropolymers) and glass products including silica glass. Preferably, container 12 is transparent. Examples of suitable transparent thermoplastic materials for container 12 include polycarbonates, polyethylene, polypropylene and polyethyleneterephthalate. Plastic materials can be oxygen-impermeable materials or may contain an oxygen-impermeable or semi-permeable layer. Alternatively, container 12 can be made of a water and air permeable plastic material.

The pressure in chamber 14 is selected to draw a predetermined volume of biological sample into chamber 14. Preferably, closure 22 is made of a resilient material that is capable of maintaining the internal pressure differential between atmospheric pressure and a pressure less than atmospheric. Closure 22 is such that it can be pierced by a needle 26 or other cannula to introduce a biological sample into container 12 as known in the art. Preferably, closure 22 is resealable. Suitable materials for closure 22 include, for example, silicone rubber, natural rubber, styrene butadiene rubber, ethylene-propylene copolymers and polychloroprene.

Suitable examples of container 12 include single-wall and multi-layer tubes. A more specific example of a suitable container 12 is disclosed in U.S. Pat. No. 5,860,937.

Container 12 may also contain a separator such as a gel, a mechanical separator or other type of separating member (e.g., filter paper or the like). Separators are useful for blood plasma preparation, specifically to separate plasma from human or animal whole blood. The gel is desirably a thixotropic polymeric gel formulation. The gel may be a homopolymer or a copolymer and may include silicone-based gels such as, for example, polysiloxanes, or organic hydrocarbon-based gels such as, for example, polyacrylics, polyesters, polyolefins, oxidized cis polybutadienes, polybutenes, blends of epoxidized soybean oil and chlorinated hydrocarbons, copolymers of diacids and propandiols, hydrogenated cyclopentadienes and copolymers of alpha-olefins with dialkylmaleates. Examples of mechanical separators that may be useful in the present invention are described in U.S. Pat. Nos. 6,516,953; 6,406,671; 6,409,528; and 6,497,325.

Container 12 may also be adapted for centrifugally separating lymphocytes and monocytes from heavier phases of a sample of whole blood. In such embodiments, the devices may also contain a liquid density gradient medium and a means for preventing mixing of the liquid density gradient medium with a blood sample prior to centrifugation. An example of a suitable lymphocyte/monocyte collection tube is disclosed in U.S. Pat. No. 5,053,134.

Aside from the embodiment illustrated in FIG. 1, other commercially available blood collection tubes suitable for use in the present invention include the following, all of which are sold by Becton, Dickinson and Company, Franklin Lakes, N.J., with all registrations and trademarks belonging to Becton, Dickinson and Company: VACUTAINER® hematology tubes (e.g., catalog nos. 367650-1, 367661, 6405, 6385, 6564, 367653, 367665, 367658, 367669, 6450-8, 6535-37 and 367662); VACUTAINER® $K_2$EDTA tubes (e.g., catalog nos. 367841-2, 367856 and 367861); VACUTAINER® PST tubes (e.g., catalog nos. 367793-4, 6698, 6595 and 6672); VACUTAINER® CPT tubes (e.g., catalog nos. 362753 and 362760-1); VACUTAINER® SST tubes (e.g., catalog nos. 367782-89, 6509-17 and 6590-92); and VACUTAINER® ACD tubes (e.g., catalog nos. 367756, 364012 and 4816), and non-evacuated BD Microtainer® Tubes with BD Microgard™ Closure (e.g., 365987, 365965, and 365974) or conventional BD Microtainer® Tubes (e.g., 365956, 365957, 365958, 365959, 365971, and 365973). Many commercial blood collection tubes have standard volumes typically ranging from 250 microliters through and including about 10.0 ml, and in some cases up to 16 ml. Typical volumes include 250, 400, and 500 microliters, as well as 2.0 ml, 3.5 ml, 4.0 ml, 5.0 ml, 8.0 ml, 8.5 ml, and 10.0 ml.

In other embodiments, the device may comprise a reservoir integrated within a testing cartridge, the reservoir capable of holding a volume of whole blood in the range of 2 through 200 microliters, more preferably 50-150 microliters. Such cartridges are sold for instance under the trade name i-STAT Point of Care System by Abbott Laboratories (Abbott Park, Ill.), and are usable with a hand-held analyzer capable of interfacing with the cartridge. Examples of such cartridges and handheld analyzers usable with the present invention include the i-STAT CHEM8+ cartridge and i-STAT® 1 handheld analyzer respectively. Such devices are taught for examples in U.S. Pat. Nos. 5,096,669, 5,112,455, 5,821,399, 5,628,961, 7,419,821, 6,750,053, and U.S. D337, 164.

Lysophospholipases (LysoPLA) are enzymes that hydrolyze lysophospholipids (LysoPL) and specifically at the carboxylic acid ester bonds, which are detergent-like intermediates in phospholipid metabolism and play essential roles in many physiological and pathological processes. Lysophosphatidylcholine (LysoPC), a normal constituent of cell membranes and which is believed to act as a lipid messenger, transducing signals initiated from membrane receptors, is an endogenous substrate for LysoPLA. Amino acid and corresponding nucleic acid sequences of human LysoPLAs are known in the art. See, e.g., U.S. Pat. Nos. 5,858,756; 6,004,792 and 7,294,496. According to one piece of evidence presented in U.S. Pat. No. 7,294,496, the LysoPLA mRNA is widely distributed in many tissues, with heart, placenta and skeletal muscle being the most abundant ones, followed by liver, pancreas, kidney, brain and lung, and in another piece of evidence (which contained messengers from more tissues), similar patterns were observed though the relative intensity for a few tissues was changed in that placenta and testis are the most abundant sources for hLysoPLA, followed by adrenal and salivary glands, liver, heart, skeletal muscle, and trachea colon. Lysophospholipases are also reported to occur in numerous isoforms.

Representative examples of LysoPLA inhibitors that may be suitable for use in the present invention include ethyl octylphosphonofluoridate, isopropyl dodecylphosphonofluoridate, n-dodecyl-benzodioxaphosphorine 2-oxide, palmitoyl carnitine, bromoenol lactone, palmityl trifluoromethyl ketone, and methyl arachidonyl fluorophosphonate (MAFP). Other inhibitors may be identified using assay methods known in the art. See, e.g., U.S. Pat. No. 7,294,496.

The LysoPLA inhibitor is present in the collection device in an effective amount to stabilize various endogenous proteins that may be present in the biological sample, e.g., ghrelin, and other proteins and peptides that require an aliphatic ester group for biological activity. Thus, aside from ghrelin, which is a marker of metabolic diseases such as diabetes, the collection devices provide for stabilization of other neuropeptides. The LysoPLA inhibitors function by inhibiting cleavage of the aliphatic ester group. Determination of the amount of the LysoPLA inhibitor to include in the blood collection device depends on several factors including potency, solubility in water, the volume of the blood collection device, and the nature and extent of non-specific interactions (e.g., due to presence of other proteins in blood such as serum albumin). Accordingly, for purposes of the present invention, the amount of the LysoPLA inhibitor (and the amounts of additional stabilization agents that may be present) is more conveniently expressed in terms of a range of concentration (from which the actual amount of the inhibitor can be easily calculated). The concentration of LysoPLA inhibitor generally ranges from about 0.1 µM to about 10 mM, and in some embodiments from about 10 uM to about 1 mM, and in some embodiments from about 100 uM to about 1 mM (i.e., 10,000,000 nM). All subranges within these ranges are also contemplated. The term "about" as used in connection with all concentration values disclosed herein refers to variability (plus/minus value) of 50%.

Although not intending to be bound by theory, the present inventors believe that the LysoPLA inhibitor may provide a dual benefit, in that in protecting the aliphatic ester group from cleavage by the LysoPLA, intrinsic proteases normally found in blood would be sterically hindered from degrading the amino acid chain of the peptide. Depending upon such factors as the nature of the analyte, the assay format and workflow (i.e., handling and storage of the collected blood sample prior to analysis), the blood collection devices of the present invention may provide stability of biochemical markers such as ghrelin for hours or even one or more days longer than similar devices that do not contain the LysoPLA inhibitor.

In some embodiments, the inventive blood collection container may include at least one additional stabilization agent, such as an inhibitor of an esterase, e.g., carboxyesterases such as butylcholinesterase and acetylcholinesterase. These stabilization agents may provide additional protection against ex-vivo degradation of proteins and peptides that require an aliphatic ester group for biological activity. Thus, aside from ghrelin, which is a marker of metabolic diseases such as diabetes, esterase inhibitors may provide enhanced stabilization of other neuropeptides. In some embodiments, however, the stabilization agent (and the device as a whole) does not include an esterase inhibitor.

Butylcholinesterase (BChE) (E.C. 3.1.1.8), also known as serum or plasma cholinesterase, is believed to play a role in the body's ability to metabolize cocaine and other drugs such as succinylcholine and aspirin. See, Lockridge, "Genetic Variants of Human Serum Butyrylcholinesterase influence the metabolism of the muscle relaxant succinylcholine." In, Kalow (ed.) *Pharmacogenetics of Drug Metabolism* New York: Pergamon Press, Inc, at pp. 15-50. BChE is normally present in human plasma in an amount of about 5 mg/l (or about 5 U/ml). BChE inhibitors useful in the present invention have a Ki value of no greater than about 0.5 µM (500 nM), or in some embodiments a Ki of not greater than about 0.05 µM (50 nM), or in yet other embodiments, a Ki of not greater than about 0.010 µM (10 nM) (and including all subranges therein). Ki's are kinetic variables (as opposed to physical properties such as molecular weight, melting and boiling points etc.) and as such, may be subject to relatively wide variation, especially depending upon the methodology used to determine this value. Thus, the term "about" as used herein in connection with Ki values refers to a variability (i.e., a plus/minus value) of 50%.

A BChE inhibitor useful in the present invention is the compound 9-amino-1,2,3,4-tetrahydroacridine, also known as tacrine (and derivatives thereof). See, U.S. Pat. No. 4,816,456. Tacrine is a centrally acting cholinesterase inhibitor approved by the FDA for the treatment of Alzheimer's disease. It is marketed by Sciele Pharma under the tradename COGNEX. Representative examples of tacrine derivatives that may be suitable for use in the present invention are taught in U.S. Pat. No. 4,754,050, as shown in the following formula:

wherein n is 1, 2 or 3; X is hydrogen, loweralkyl, loweralkoxy, halogen, hydroxy, nitro, trifluoromethyl, NHCOR$_2$ where R$_2$ is loweralkyl, or NR$_3$R$_4$ where R$_3$ and R$_4$ are independently hydrogen or loweralkyl; R is hydrogen or loweralkyl; R$_1$ is hydrogen, loweralkyl, diloweralkylaminoloweralkyl, arylloweralkyl, diarylloweralkyl, furylloweralkyl, thienylloweralkyl, oxygen-bridged arylloweralkyl, oxygen-bridged diarylloweralkyl, oxygen-bridged furylloweralkyl or oxygen-bridged thienylloweralkyl; Y is C=O or CR$_5$OH where R$_5$ is hydrogen or loweralkyl; Z is CH$_2$ or C=CR$_6$R$_7$ where R$_6$ and R$_7$ are independently hydrogen or lower alkyl; or Y and Z taken together is CR$_5$=CH where CR$_5$ and CH correspond to Y and Z respectively; an optical antipode thereof, or a pharmaceutically acceptable acid addition salt thereof.

Specific tacrine derivatives embraced by this formula include the following:
9-Amino-3,4-dihydroacridin-1(2H)-one; 9-Amino-3,4-dihydro-6-methylacridin-1(2H)-one; 9-Amino-3,4-dihydro-6-methoxyacridin-1(2H)-one; 9-Amino-3,4-dihydro-6-fluoroacridin-1(2H)-one; 9-Amino-6-chloro-3,4-dihydroacridin-1(2H)-one; 9-Amino-7-chloro-3,4-dihydroacridin-1(2H)-one; 9-Amino-3,4-dihydro-6-trifluoromethylacridin-1(2H)-one; 9-Amino-3,4-dihydro-7-nitroacridin-1(2H)-one; 7,9-Diamino-3,4-dihydroacridin-1(2H)-one; N-[9-Amino-3,4-dihydro-1(2H)-oxoacridin-7-yl]acetamide; 3,4-Dihydro-9-methylaminoacridin-1(2H)-one; 3,4-Dihydro-9-methylamino-7-nitroacridin-1(2H)-one; 3,4-Dihydro-9-propylaminoacridin-1(2H)-one; 3,4-Dihydro-9-[2-(dimethylamino)ethyl]aminoacridin-1(2H)-one;

9-Benzylamino-3,4-dihydroacridin-1(2H)-one; 9-Benzylamino-3,4-dihydro-6-methylacridin-1(2H)-one; 9-Benzylamino-3,4-dihydro-6-fluoroacridin-1(2H)-one; 9-Benzylamino-6-chloro-3,4-dihydroacridin-1(2H)-one; 9-Benzylamino-3,4-dihydro-6-trifluoromethylacridin-1(2H)-one; 3,4-Dihydro-9-(2-methylbenzylamino)acridin-1(2H)-one; 3,4-Dihydro-9-(3-methylbenzylamino)acridin-1(2H)-one; 3,4-Dihydro-9-(4-methylbenzylamino)acridin-1(2H)-one; 3,4-Dihydro-9-(2-methoxybenzylamino)acridin-1(2H)-one; 3,4-Dihydro-9-(3-methoxybenzylamino)acridin-1(2H)-one; 3,4-Dihydro-9-(4-methoxybenzylamino)acridin-1(2H)-one; 3,4-Dihydro-9-(2-fluorobenzylamino)acridin-1(2H)-one; 3,4-Dihydro-9-(3-fluorobenzylamino)acridin-1(2H)-one; 3,4-Dihydro-9-(4-fluorobenzylamino)acridin-1(2H)-one; 6-Chloro-3,4-dihydro-9-(4-fluorobenzylamino)acridin-1(2H)-one; 9-(2-Chlorobenzylamino)-3,4-dihydroacridin-1(2H)-one; 9-(3-Chlorobenzylamino)-3,4-dihydroacridin-1(2H)-one; 9-(4-Chlorobenzylamino)-3,4-dihydroacridin-1(2H)-one; 3,4-Dihydro-9-[(2,3,4,5,6-pentafluorobenzyl)amino]acridin-1(2H)-one; 3,4-Dihydro-9-(2-trifluoromethylbenzylamino)acridin-1(2H)-one; 3,4-Dihydro-6-fluoro-9-(2-trifluoromethylbenzylamino)acridin-1(2H)-one; 3,4-Dihydro-9-(3-trifluoromethylbenzylamino)acridin-1(2H)-one; 3,4-Dihydro-9-(4-trifluoromethylbenzylamino)acridin-1(2H)-one; 3,4-Dihydro-9-phenethylaminoacridin-1(2H)-one; 3,4-Dihydro-9-(4,4-diphenylbutyl)aminoacridin-1(2H)-one; 3,4-Dihydro-9-(4,4-diphenylbutylamino)-6-trifluoromethylacridin-1(2H)-one; 9-[4,4-Bis(3-fluorophenyl)butylamino]-3,4-dihydroacridin-1(2H)-one; 9-[4,4-bis(4-fluorophenyl)butylamino]-3,4-Dihydroacridin-1(2H)-one; 3,4-Dihydro-9-(3-phenoxypropylamino)acridin-1(2H)-one; 9-[2-[Bis(4-fluorophenyl)methoxy]ethylamino-3,4-dihydroacridin-1(2H)-one; 9-[4-(Benzyloxy)benzylamino]-3,4-dihydroacridin-1(2H)-one; 3,4-Dihydro-9-[(2-thienyl)methylamino]acridin-1(2H)-one; 9-Amino-2,3-dihydro-cyclopenta[b]quinolin-1-one; 9-Amino-1,2,3,4-tetrahydroacridin-1-ol; 9-Amino-6-chloro-1,2,3,4-tetrahydroacridin-1-ol; 9-Amino-7-chloro-1,2,3,4-tetrahydroacridin-1-ol; 9-Amino-6-methoxy-1,2,3,4-tetrahydroacridin-1-ol; 9-Amino-6-fluoro-1,2,3,4-tetrahydroacridin-1-ol; 9-Amino-1,2,3,4-tetrahydro-6-trifluoromethylacridin-1-ol; 9-Methylamino-1,2,3,4-tetrahydroacridin-1-ol; 9-Propylamino-1,2,3,4-tetrahydroacridin-1-ol; 9-[2-(Dimethylamino)ethyl]amino-1,2,3,4-tetrahydroacridin-1-o; 9-Benzylamino-1,2,3,4-tetrahydroacridin-1-ol; 9-Benzylamino-6-methyl-1,2,3,4-tetrahydroacridin-1-ol; 9-Benzylamino-6-fluoro-1,2,3,4-tetrahydroacridin-1-ol; 9-Benzylamino-6-chloro-1,2,3,4-tetrahydroacridin-1-ol; 9-Benzylamino-1,2,3,4-tetrahydro-6-trifluoromethylacridin-1-o; 9-(2-Methylbenzylamino)-1,2,3,4-tetrahydroacridin-1-ol; 9-(3-Methylbenzylamino)-1,2,3,4-tetrahydroacridin-1-ol; 9-(4-Methylbenzylamino)-1,2,3,4-tetrahydroacridin-1-ol; 9-(2-Methoxybenzylamino)-1,2,3,4-tetrahydroacridin-1-ol; 9-(3-Methoxybenzylamino)-1,2,3,4-tetrahydroacridin-1-ol; 9-(4-Methoxybenzylamino)-1,2,3,4-tetrahydroacridin-1-ol; 9-(2-Fluorobenzylamino)-1,2,3,4-tetrahydroacridin-1-ol; 9-(3-Fluorobenzylamino)-1,2,3,4-tetrahydroacridin-1-ol; 9-(4-Fluorobenzylamino)-1,2,3,4-tetrahydroacridin-1-ol; 6-Chloro-9-(4-fluorobenzylamino)-1,2,3,4-tetrahydroacridin-1-ol; 9-(2-Chlorobenzylamino)-1,2,3,4-tetrahydroacridin-1-ol; 9-(3-Chlorobenzylamino)-1,2,3,4-tetrahydroacridin-1-ol; 9-(4-Chlorobenzylamino)-1,2,3,4-tetrahydroacridin-1-ol; 1,2,3,4-Tetrahydro-9-(2-trifluoromethylbenzyl)aminoacridin-1-ol; 6-Fluoro-1,2,3,4-tetrahydro-9-(2-trifluoromethylbenzylamino)acridin-1-ol; 1,2,3,4-Tetrahydro-9-(3-trifluoromethylbenzylamino)acridin-1-ol; 1,2,3,4-Tetrahydro-9-(4-trifluoromethylbenzylamino)acridin-1-ol; 9-[(2,3,4,5,6-Pentafluorobenzyl)amino]-1,2,3,4-tetrahydroacridin-1-ol; 9-Phenethylamino-1,2,3,4-tetrahydroacridin-1-ol; 9-(4,4-Diphenylbutyl)amino-1,2,3,4-tetrahydroacridin-1-ol; 9-[4,4-Bis(3-fluorophenyl)butylamino]-1,2,3,4-tetrahydroacridin-1-ol; 9-[4,4-Bis(4-fluorophenyl)butylamino]-1,2,3,4-tetrahydroacridin-1-ol; 9-(3-Phenoxypropylamino)-1,2,3,4-tetrahydroacridin-1-ol; 9-[[2-[Bis(4-fluorophenyl)methoxy]ethyl]amino]-1,2,3,4-tetrahydroacridin-1-ol; 9-[4-(Benzyloxy)benzylamino]-1,2,3,4-tetrahydroacridin-1-ol; 9-[(2-Thienyl)methylamino]-1,2,3,4-tetrahydroacridin-1-ol; 9-Amino-3,4-dihydroacridine; 9-Amino-1-methyl-1,2,3,4-tetrahydroacridin-1-ol; 9-Amino-3,4-dihydro-2-methyleneacridin-1(2H)-one; 9-Amino-1,2,3,4-tetrahydro-cyclopenta[b]quinolin-1-ol; 2-(3-Oxoclohexen-1-yl)aminobenzonitrile; and 4-Chloro-2-(3-oxocyclohexen-1-yl)aminobenzonitrile.

Other butyrylcholinesterase inhibitors that may be suitable for use in the present invention include tacrine dimmers such as ethopropazine (i.e., N,N,N-diethyl-α-methyl-10H-phenothiazine-10-ethanamine; 10-(2-diethylamino-2-methylethyl)phenothiazine; or phenopropazine), and derivatives thereof. See, e.g., U.S. Pat. Nos. 2,607,773 and 4,833,138. Ethopropazine, hydrochloride salt, has been approved by the FDA for use in treatment of Parkinson's disease.

Yet other butyrylcholinesterase inhibitors include hybrids of tacrine and (−)-huperzine A (which is an enantiomeric lycodine alkaloid isolated from the club moss *Huperzia serrata* of the *Lycopodium* species, Huperziaceae). Examples of Huperzine A-tacrine hybrids are known in the art as Compounds 5a, 5b and 5c, and Huprine X. Their corresponding chemical names are as follows: ((9E)-N1-(7-(1,2,3,4-tetrahydroacridin-9-ylamino)heptyl)-9-ethylidene-4,4,7-trimethylbicyclo[3.3.1]non-6-ene-1,3-diamine) (5a); ((9E)-N1-(7-(1,2,3,4-tetrahydroacridin-9-ylamino)heptyl)-9-ethylidene-47-methylbicyclo[3.3.1]non-6-ene-1,3-diamine) (5b); ((9E)-N1-(7-(1,2,3,4-tetrahydroacridin-9-ylamino)heptylamino)-9-ethylidene-3-methylbicyclo[3.3.1]non-3-ene-1-carboxylic Acid Methyl Ester) (5c); and (1S)-7-chloro-15-ethyl-10-azatetracyclo[11.3.1.0^{2,11}].0^{4,9}]heptadeca-2(11),3,5,7,9,14-hexaen-3-amine) (Huprine X). Methods of synthesizing these compounds are disclosed in Gemma, et al., J. Med. Chem. 49(11):3421-25 (2006) (5a, 5b and 5c), and Camps, et al., Mol. Pharmacol. 57:409-17 (2000) (Huprine X).

The concentration of BChE generally ranges from about 5 µM to about 500 mM (i.e., $5 \times 10^8$ nM), and in some embodiments ranges from about 0.5 µM to about 50 mM, and in yet other embodiments, from about 0.1 µM to about 10 mM. All subranges within these ranges are also contemplated. As in the case of the Ki values, the term "about" as used in connection with all concentration values disclosed herein refers to variability (plus/minus value) of 50%.

The stabilization agent may also include an inhibitor of another type of serum esterase, and specifically an inhibitor of another B-esterase (of which BChE is a member). These esterases include acetylcholinesterase (AChE) (EC 3.1.1.7) and nonspecific carboxylesterase (EC 3.1.1.1). Inhibitors of AChE act upon cholinesterase and inhibit it from breaking down the acetylcholine which functions in the body as a neurotransmitter. Some BChE inhibitors such as tacrine and huperazine A are known to inhibit acetylcholinesterase as well. Tacrine has a reported Ki for AChE of 6.9 nm (Bencharit, et al., Chem. Biol. 10:341-9 (2003)). Huperzine A has a reported Ki for AChE of 47 nm (Gemma, et al., J. Med. Chem. 49:3421-5 (2006)). Given that BChE constitutes a significant portion of total esterase activity in human serum (i.e., about 5 mg/L of BChE compared to 0.008 mg/L for AChE), the inclusion of inhibitors in the blood collection tube is optional.

The Ki's of the AChE inhibitors suitable for use in the present invention are typically about 500 nm or less, and in other embodiments, less than about 400 nm, 300 nm, 200 nm, 100, nm, 50 nm or 10 nm. As disclosed herein, Ki values for a given AChE inhibitor can be determined in accordance with standard assay techniques.

Thus, other AChE inhibitors that may be useful in the present invention include the following: Huprine X ((1S)-7-chloro-15-ethyl-10-azatetracyclo[11.3.1.0^{2,11}.0^{4,9}]heptadeca-2(11),3,5,7,9,14-hexaen-3-amine) (Ki of 0.026 nm); Tacrine Dimer 4a (methylbis[3-(1,2,3,4-tetrahydroacridin-9-ylamino)propyl]amine) (Ki of 0.06 nm); Tacrine Dimer 4d (2-{bis[3-(1,2,3,4-tetrahydroacridin-9-ylamino)propyl]amino}ethan-1-ol | N,N-Bis[3-[(1,2,3,4-tetrahydroacridin-9-yl)amino]propyl]-N-hydroxyethylamine) (Ki of 0.65 nm); Tacrine derivative 2 (6,8-dichloro-1,2,3,4-tetrahydroacridin-9-amine) (Ki of 1.0 nm); Tacrine Dimer 3b (Homodimeric Tacrine Analog 3b | N-[7-(1,2,3,4-tetrahydroacridin-9-ylamino)heptyl]-1,2,3,4-tetrahydroacridin-9-amine | tacrine homobivalent compound 3a) (Ki of 1.3 nm); Tacrine Dimer 4c (N,N-Bis[3-[(1,2,3,4-tetrahydroacridin-9-yl)amino]propyl]-N-allylamine | prop-2-en-1-ylbis[3-(1,2,3,4-tetrahydroacridin-9-ylamino)propyl]amine) (Ki of 1.6 nm); Tacrine Dimer 3c (Homodimeric Tacrine Analog 3c | N-[8-(1,2,3,4-tetrahydroacridin-9-ylamino)octyl]-1,2,3,4-tetrahydroacridin-9-amine) (Ki of 1.9 nm); Tacrine Dimer 4b (N,N-Bis[3-[(1,2,3,4-tetrahydroacridin-9-yl)amino]propyl]-N-ethylamine | ethylbis[3-(1,2,3,4-tetrahydroacridin-9-ylamino)propyl]amine) (Ki of 2.8 nm); tacrine heterobivalent compound 3c (N-{7-[(6,8-dichloro-1,2,3,4-tetrahydroacridin-9-yl)amino]heptyl}-1,2,3,4-tetrahydroacridin-9-amine) (Ki of 6.0 nm); Huperzine A-Tacrine Hybrid 5c ((9E)-7-(7-(1,2,3,4-Tetrahydroacridin-9-ylamino)heptylamino)-9-ethylidene-3-methylbicyclo[3.3.1]non-3-ene-1-carboxylic Acid Methyl Ester | methyl (1S)-9-ethylidene-3-methyl-7-{[7-(1,2,3,4-tetrahydroacridin-9-ylamino)heptyl]amino}bicyclo[3.3.1]non-3-ene-1-carboxylate) (Ki of 6.4 nm); Tacrine Dimer 4j (N-Methyl-N-(1,2,3,4-tetrahydroacridin-9-yl)-N-[3-(1,2,3,4-tetrahydroacridin-9-ylsulfanyl)propyl]-1,3-propanediamine | methyl[3-(1,2,3,4-tetrahydroacridin-9-ylamino)propyl][3-(1,2,3,4-tetrahydroacridin-9-ylsulfanyl)propyl]amine) (Ki of 9.1 nm); Huperzine A-Tacrine Hybrid 5b ((9E)-N1-(7-(1,2,3,4-Tetrahydroacridin-9-ylamino)heptyl)-9-ethylidene-7-methylbicyclo[3.3.1]non-6-ene-1,3-diamine | N-(7-{[(1S)-1-amino-9-ethylidene-7-methylbicyclo[3.3.1]non-6-en-3-yl]amino}heptyl)-1,2,3,4-tetrahydroacridin-9-amine) (Ki of 15.70 nm); Huperzine A-Tacrine Hybrid 5a (9E)-N1-(7-(1,2,3,4-Tetrahydroacridin-9-ylamino)heptyl)-9-ethylidene-4,4,7-trimethylbicyclo[3.3.1]non-6-ene-1,3-diamine | N-(7-{[(1S)-1-amino-9-ethylidene-4,4,7-trimethylbicyclo[3.3.1]non-6-en-3-yl]amino}heptyl)-1,2,3,4-tetrahydroacridin-9-amine) (Ki of 16.50 nm); AP2238 3-(4-{[Benzyl(methyl)amino]methyl}-phenyl)-6,7-dimethoxy-2H-2-chromenone | 3-(4-{[benzyl(methyl)amino]methyl}phenyl)-6,7-dimethoxy-2H-chromen-2-one) (Ki of 21.70 nm); Tacrine Dimer 4i (N-(1,2,3,4-Tetrahydroacridin-9-yl)-N-[8-(1,2,3,4-tetrahydroacridin-9-yl)oct-1-yl]amine | N-[8-(1,2,3,4-tetrahydroacridin-9-yl)octyl]-1,2,3,4-tetrahydroacridin-9-amine) (Ki of 30 nm); tacrine heterobivalent compound 3g (6,8-dichloro-N-[7-(1,2,3,4-tetrahydroacridin-9-ylsulfanyl)heptyl]-1,2,3,4-tetrahydroacridin-9-amine) (Ki of 41 nm); Tacrine Dimer 4m (N-[3-(1,2,3,4-Tetrahydroacridin-9-ylamino)propyl]-N-[4-(1,2,3,4-tetrahydroacridin-9-ylsulfanyl)butyl]acetamide) (Ki of 47 nm); 9-Amino-6-Chloro-2-Methoxyacridine (6-chloro-2-methoxyacridin-9-amine) (Ki of 49 nm); Tacrine Dimer 4k (N-[3-(1,2,3,4-Tetrahydroacridin-9-ylamino)propyl]-N-[3-(1,2,3,4-tetrahydroacridin-9-ylsulfanyl)propyl]acetamide) (Ki of 50 nm); tacrine heterobivalent compound 3i (N-[6-(1,2,3,4-tetrahydroacridin-9-ylsulfanyl)hexyl]-1,2,3,4-tetrahydroacridin-9-amine) (Ki of 100 nm); tacrine homobivalent compound 3b (6,8-dichloro-N-{7-[(6,8-dichloro-1,2,3,4-tetrahydroacridin-9-yl)amino]heptyl}-1,2,3,4-tetrahydroacridin-9-amine) (Ki of 150 nm); Tacrine Dimer 3a (N-[5-(1,2,3,4-tetrahydroacridin-9-ylamino)pentyl]-1,2,3,4-tetrahydroacridin-9-amine) (Ki of 210 nm); Tacrine Dimer 4g (N-[8-(1,2,3,4-tetrahydroacridin-9-ylsulfanyl)octyl]-1,2,3,4-tetrahydroacridin-9-amine) (Ki of 250 nm); tacrine heterobivalent compound 3f (N-{7-[(6,8-dichloro-1,2,3,4-tetrahydroacridin-9-yl)sulfanyl]heptyl}-1,2,3,4-tetrahydroacridin-9-amine) (Ki of 290 nm); 1,2-Dione-Based Compound, 8 (1,2-dihydronaphthalene-1,2-dione | 1,2-naphthoquinone) (Ki of 320 nM); Tacrine Dimer 4f (N-[7-(1,2,3,4-tetrahydroacridin-9-ylsulfanyl)heptyl]-1,2,3,4-tetrahydroacridin-9-amine | tacrine heterobivalent compound 3e) (Ki of 340 nm); and 6,9-Diamino-2-Ethoxyacridine (7-ethoxyacridine-3,9-diamine) (Ki of 490 nm). Ki values disclosed herein for the forementioned AChE inhibitors are reported in Gemma, et al., J. Med. Chem. 49:3421-5 (2006); Campiani, et al., J. Med. Chem. 48:1919-29 (2005); Wong, et al., J. Am. Chem. Soc. 125:363-73 (2003); Savini, et al., Bioorg. Med. Chem. Lett. 11:1779-82 (2001); Piazzi, et al., J. Med. Chem. 46:2279-82 (2003); Bencharit, supra.; and Hyatt, et al., J. Med. Chem. 50:5727-34 (2007).

Even further examples of AChE inhibitors that may be useful in the present invention include the following: organophosphates (e.g., Metrifonate, Echothiophate, diisopropyl fluorophosphates, Cyclosarin, Dimethoate, Sarin, Soman, Tabun, VX, VE, VG, VM, Diazinon, Malathion and Parathion); carbamates (e.g., Physostigmine, Neostigmine, Pyridostigmine, Ambenonium, Demarcarium, Rivastigmine, Aldicarb, Bendiocarb, Bufencarb, Carbaryl, Carbendazim, Carbetamide, Carbofuran, Chlorbufam, Chloropropham, Ethiofencarb, Formetanate, Methiocarb, Methomyl, Oxamyl, Phenmedipham, Pinmicarb, Pirimicarb, Propamocarb, Propham and Propoxur); Penanthrene derivatives (e.g., galantamine); piperidines (e.g., Donepezil (E2020) (Ki of 2.9 nm)); Edrophonium; and natural compounds (e.g., galantamine and Onchidal).

Since some BChE inhibitors also exhibit potent AChE inhibitory activity, embodiments of the present invention may include a single esterase inhibitor that possesses both BChE and AChE inhibitory activities.

The concentration of the additional serum esterase inhibitor that may be present in the blood collection device generally ranges from about 0.1 µM to about 70 mM, and in some embodiments, from about 1 mM to about 7 mM.

The stabilization agent may also include a protease inhibitor. Protease inhibitors useful in the present invention exhibit inhibitory activity against one or more classes of proteases including, for example, serine proteases, exopeptidases and dipeptidyl peptidases. Thus, the device may contain a cocktail of two or more of such inhibitors, including for example, an inhibitor of a serine protease and an inhibitor of an exopeptidase, an inhibitor of a serine protease and an inhibitor of a dipeptidyl peptidase, an inhibitor of an exopeptidase and an inhibitor of a dipeptidyl peptidase, and an inhibitor of a serine protease, an inhibitor of an exopeptidase and an inhibitor of a dipeptidyl peptidase. See, e.g., U.S. Pat. No. 7,309,468, to Stevens, et al.

Representative examples of serine protease inhibitors include antipain, aprotinin, antithrombin, chymostatin, DFP, elastatinal, APMSF, phenylmethylsulfonyl fluoride (PMSF), AEBSF, TLCK, TPCK, leupeptin, trypsin and soybean trypsin inhibitor. Concentrations of serine protease inhibitors generally range from about 0.1 µM to about 100 µM.

Representative examples of exopeptidase inhibitors that may be useful in the present invention include amastatin, bestatin, diprotin A and diprotin B. Concentrations of exopeptidase inhibitors generally range from about 0.01 mM to about 1 mM.

Dipeptidyl peptidase activity (which includes DPP-IV and DPP-IV-like activities) present in the circulation is highly specific in releasing dipeptides from the N-terminal end of biologically active peptides with proline or alanine in the penultimate position of the N-terminal sequence of the peptide substrate. The glucose-dependent insulinotropic polypeptides $GIP_{1-42}$ and $GLP-1_{7-36}$, potentiate glucose-induced insulin secretion from the pancreas (incretins), are substrates of DPP-IV. The DPP-IV enzyme releases the dipeptides tyrosinyl-alanine and histidyl-alanine, respectively, from the N-termini of these peptides both in vitro and in vivo. Mentlein, et al., Eur. J. Biochem. 214, 829 (1993). Representative examples of inhibitors of dipeptidyl peptidase IV (DPP-IV) that may be useful in the present invention include vildagliptin, sitagliptin, saxagliptin, linagliptin and alogliptin. Other DPP-IV inhibitors include dipeptide compounds formed from an amino acid such as isoleucine, Asn, Asp, Glu, His, Pro, and Val, and a thiazolidine or pyrrolidine group, and sterioisomers e.g., L-threo and L-allo forms thereof, and inorganic and organic salts thereof (e.g., phosphate, sulfate, acetate, tartarate, succinate and fumarate) Specific examples of the dipeptide compounds include L-threo-isoleucyl thiazolidide, L-allo-isoleucyl thiazolidide, L-threo-isoleucyl pyrrolidide, and L-allo-isoleucyl pyrrolidide. Concentrations of dipeptidyl peptidase inhibitor generally range from about 0.01 mM to about 1 mM.

The stabilization agent may further contain inhibitors of other classes of proteases. Thus, in further embodiments, the blood collection devices may also contain an inhibitor of a cysteine protease (e.g., IAA (indoleacetic acid) and E-64), a serine/cysteine protease (e.g., leupeptin, TPCK, PLCK-HCL, 2-heptanone-HCL, and antipain-HCl), an aspartic protease (e.g., pepstatin, and VdLPFFVdL), a metalloprotease (e.g., EDTA, bestatin, 1,10-phenanthroline and phosphoramodon), a thiol protease, an aspartic/calpain protease (e.g., pepstatin, N-acetyl-leu-leu-norleucinal and N-acetyl-leu-leu-methioninal), a caspase, an endopeptidase (e.g., $\alpha_2$-macroglobulin (referred to as an universal endopeptidase inhibitor), $\alpha_1$-anti-trypsin and thiorphan), and combinations of two or more thereof. Additional examples of protease inhibitors include soybean or lima bean trypsin inhibitor, pancreatic protease inhibitor, egg white ovostatin and egg white cystatin. Persons skilled in the field of proteomics appreciate that a given inhibitor may exhibit inhibitory activity against one or more proteases in the same class of proteases, as well as inhibitory activity against one or more proteases in different classes of proteases. Bestatin and amastatin, for example, exhibit inhibitory activity against metalloproteases as well as exopeptidases.

Embodiments of the present invention that employ a plurality of stabilization agents, e.g., in addition to a LysoPLA inhibitor a protease inhibitor, or a BChE inhibitor and a protease inhibitor), are also referred to herein as a stabilization agent cocktail.

The stabilization agent may be present in any suitable form, including liquids (e.g., solutions and suspensions) and solids (e.g., pellet, tablet, capsule, spray-dried material, freeze-dried material, powder, particle, crystals and lyophilized material) and semi-solids (e.g., gel). Lyophilization may be particularly useful in that it provides good stability (e.g., in terms of maximizing shelf-life of the stabilization agent) and also allows for subsequent sterilization. For example, the stabilizing agent may be introduced into the container of the device in the form of a liquid composition, and then lyophilized by standard techniques. Freeze-drying, for example, entails freezing the liquid composition and then slowly warming after freezing, while simultaneously applying a vacuum, such that a freeze-dried powder remains in the collection device. Various additives such as PVP or trehalose may be added to the liquid composition prior to freeze-drying to facilitate pelletizing of the stabilization agent and reconstitution of the lyophilized agents upon contact with blood. Vacuum drying may also be used after adding the liquid composition. In other embodiments, the stabilizing agent is formed into a liquid or solid aerosol and sprayed onto one or more surfaces of the interior of the container. Encapsulating or formulating the stabilization agent in the form of a tablet protects it from light exposure and prevent other undesirable interactions between the inhibitors and other elements in the container. Encapsulation materials and excipients useful in making tablets and capsules that dissolve upon sample collection are well known in the art.

In addition to being disposed in the reservoir, the stabilization agent may be located on any surface of the collection device that comes into contact with the collected blood. For example, the stabilization agent may also be located on stoppers and seals for closing the device, or on mechanical, or other inserts placed within the device.

In addition to the stabilization agent, the device of the present invention may also contain carrier media (e.g., water or alcohol), stabilizing or reconstitution media (e.g., polyvinylpyrollidone, trehalose, mannitol, etc.) and/or one or more other additives for treating the biological sample. Typical additives include phenol, phenol/chloroform mixtures, alcohols, aldehydes, ketones, organic acids, salts of organic acids, alkali metal salts of halides, organic chelating agents, fluorescent dyes, antibodies, binding agents, anticoagulants such as sodium citrate, heparin, EDTA and its salts (e.g., potassium EDTA), antioxidants, reducing agents and buffering agent. Preferably, the carrier and additives do not degrade proteins. Where the inhibitors are in tablet form, pharmaceutical tablet disintegrating materials, which are known to those skilled in the art, may be included, if desired.

A useful manufacturing process for a device of the present invention involves obtaining a collection container, such as a tube; adding the stabilization agent (e.g., a LysoPLA inhibitor and a protease inhibitor) to the container; lyophilizing the inhibitors; evacuating the container; and sterilizing the container. A separating member may be added to the container, if desired. An example of a suitable lyophilization/evacuation process is as follows: the container is frozen at a temperature of about −40° C. at a pressure of about 760 mm for about 6 to 8 hours; the container is dried as the temperature is increased from −40° C. to about 25° C., at a pressure of about 0.05 mm, for about 8 to 10 hours; and the container is then evacuated at a temperature of about 25° C. and a pressure of about 120 mm for about 0.1 hours. Preferably, the sterilization technique is with cobalt 60 radiation.

The whole blood or component(s) thereof may be withdrawn from the patient directly into the blood collection device without any intervening process steps. It has been found that collecting the whole blood directly from the patient, and introducing the sample directly into the device containing the stabilization agent substantially prevents the degradation and/or fragmentation of proteins that otherwise occurs when the sample is stored before combining it with the stabilization agent. The method of the present invention is useful both with open collection devices and with closed collection devices wherein the opening is closed by a closure means.

In a preferred embodiment, the collection device is a tube which is used for drawing a whole blood sample directly from a patient for stabilizing the proteins immediately at the point of collection. The collection tube may be an evacuated system for collecting blood. Alternatively, the tube may be a partially-evacuated or a non-evacuated system for collecting blood. A suitable example of an evacuated system is a closed tube. A manual syringe draw is a suitable example of both a partially-evacuated and a non-evacuated system. Non-evacuated systems may also include automatic draw systems. Evacuated systems are particularly preferred.

The blood collection devices of the present invention are particularly suited for stabilizing proteins that contain aliphatic ester side chains, such as ghrelin, and in the embodiments that include a protease inhibitor, additional protein biomarkers of disease, e.g., GLP-1, GIP and glucagon, which are also biomarkers for metabolic diseases such as diabetes. Thus, the collection devices may be used to provide reliable standards in which to facilitate design of assays such as ELISA that will allow for detection of these proteins in the range of $10^{-9}$-$10^{-11}$ M, which includes circulating levels of these proteins in healthy individuals as well as therapeutic levels. Thus, in addition to methods of diagnosing a disease such as a metabolic disorder (wherein elevated levels of the marker relative to a control (such as established medical criteria and/or a concentration range derived from a statistically significant population of nonpathological donors) is indicative of the presence of disease), they may allow for methods for monitoring therapy in a patient suffering from diseases such as metabolic disorders, wherein normalization (or a trend toward normalization) of amounts of these proteins is indicative of successful therapy.

The blood collection devices of the present invention may also be used for the purposes of collecting and storing blood from patients who have been ingesting prodrugs that are acylated (also referred to herein as prodrugs bearing aliphatic ester side chains), for therapeutic purposes, e.g., as part of a treatment regimen for a disease or inflammatory condition. A prodrug is generally understood to mean an active drug agent that is actually a precursor form of a drug that is therapeutically inactive or significantly less active than the active moiety of the agent (which may be a metabolite). Upon administration such as oral ingestion, many prodrugs are converted to the active drug/metabolite via cleavage of an ester bond via intrinsic lysophospholipases. For example, enalapril is converted to the active metabolite enalaprilat, and the prodrug valacyclovir is converted to the active drug/metabolite acyclovir. Heroin is deacetylated to the active drug/metabolite morphine. In clinical settings, and in particular clinical trials, it is advantageous to monitor the blood levels of the prodrug as well as the active metabolite in patients over the course of time, e.g., from one or more of the standpoints of safety, efficacy, bioactivity and bioequivalence.

For example, in bioactivity studies, which measure the rate and extent to which the active ingredient or active moiety is absorbed from a drug product and becomes available at the site of action, it is recommended that the concentration and activity of both the parent drug and the metabolite are determined. In bioequivalence studies (which study the extent of difference in the rate and extent to which ingredient or active moiety in pharmaceutical equivalents or alternatives becomes available at the site of drug action when administered at the same molar dose under similar conditions), measurement of the parent (prodrug) form is generally recommended (except in situations in which the parent drug levels are too low to allow reliable analytical measurement in blood, serum or plasma for an adequate length of time, or when the metabolite contributes meaningfully to safety and/or efficacy, in which cases, the concentration and activity of both the prodrug and the metabolite are measured).

Qualitative or quantitative analysis of blood collected from patients who have been on such therapy (which includes patients who are currently undergoing such therapy) using the inventive blood collection devices enhances accuracy of any such analysis in that ex vivo esterase-catalyzed degradation of the prodrug in the collected blood is inhibited during storage. Processing of the blood samples, e.g., extraction of plasma from the collected blood, and separation of the prodrug and the active metabolite, and subsequent measurement of these entities may be conducted in accordance with standard techniques. For example, the prodrug and active metabolite may be separated by reverse-phase HPLC. Detection of presence or relative amounts of the prodrug and active metabolite may be conducted in accordance with standard techniques such as mass spectrometry, followed by analysis of the results, e.g., by weighted quadratic or linear regression. See, e.g., Wiltshire, et al., J. Chromatogr. B745:373-88 (2000) (and references cited therein). Controls to which the measured values may be compared include calibration and quality control samples (referred to in Wiltshire, supra, as calibration curves).

The present invention will now be described by reference to the following non-limiting examples. Unless otherwise stated, all parts and percents are based on weight.

EXAMPLE 1

Comparative Stability of Ghrelin in Plasma Samples

Figure 2:
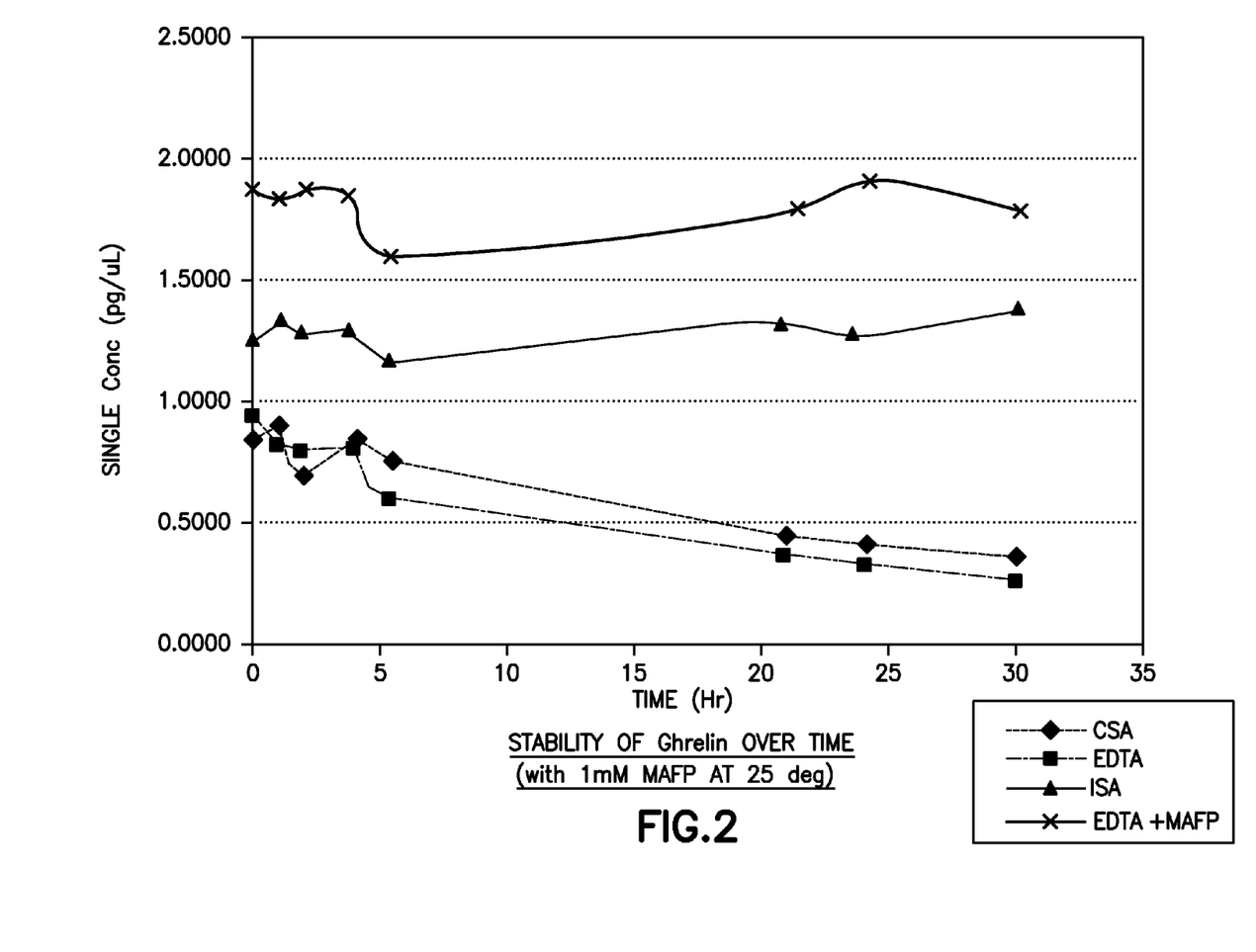
FIG. 2 is a graph that displays a comparison of acyl-ghrelin stability over 30 hrs in four different blood collection tubes containing: 1) the LysoPLA inhibitor methyl arachidonyl fluorophosphonate (MAFP), EDTA, the esterase inhibitor, tacrine, and the protease inhibitors L-threo-isoleucyl thiazolidide, bestatin and leupeptin (an inventive stabilization agent "ISA", designated in the figure as ▲); 2) another inventive stabilization agent that included the anticoagulant EDTA and MAFP (designated in the figure as x); 3) EDTA and the esterase inhibitor and the protease inhibitors (the comparative stabilization agent "CSA" designated in the figure as ◆); and 4) EDTA alone (designated in the figure as ■), followed by spiking with 1 pg/uL acyl-ghrelin.

Blood was collected in 4 separate tubes containing 1) the LysoPLA inhibitor methyl arachidonyl fluorophosphonate (MAFP), EDTA, the esterase inhibitor, tacrine, and the protease inhibitors L-threo-isoleucyl thiazolidide, bestatin and leupeptin (an inventive stabilization agent "ISA", designated in the figure as ▲), 2) another inventive stabilization agent that includes the anti-coagulant EDTA and MAFP (designated in the figure as x), 3) EDTA and the esterase inhibitor and the protease inhibitors (the comparative stabilization agent "CSA" designated in the figure as ♦), and 4) EDTA alone (designated in the figure as ■), followed by spiking 1 pg/uL acyl-ghrelin. All four tubes were drawn indirectly from the same subject for this experiment and processed identically. The data illustrated in FIG. 2 clearly indicate that in tubes 3 and 4 acyl-ghrelin was being degraded over time. However, the two tubes (Nos. 1 and 2) containing MAFP showed stabilization over the 30 hr plasma incubation time. Tube 2, which contained MAFP and EDTA, outperformed tube 1 that contained the esterase inhibitor and the protease inhibitors.

Figure 3:
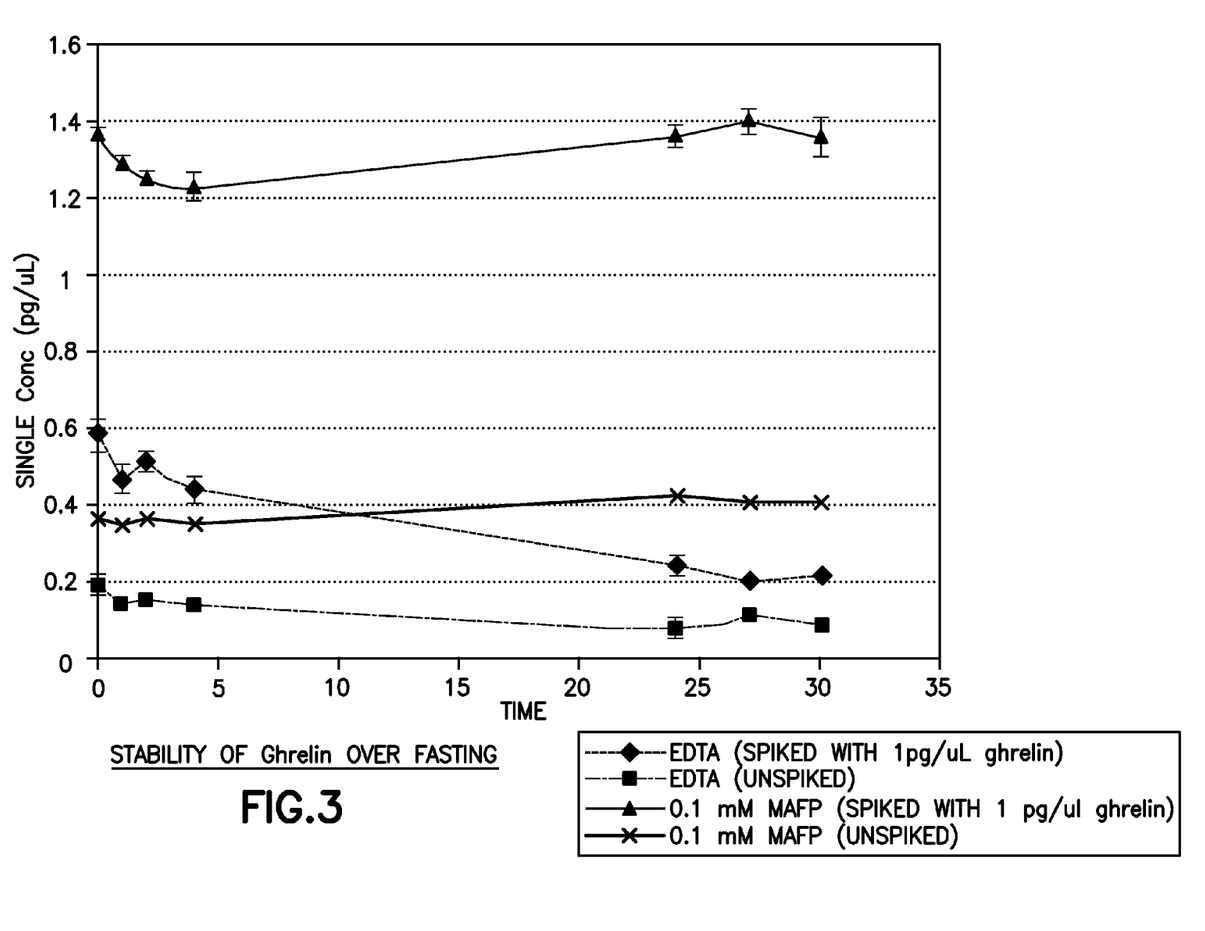
FIG. 3 is a graph that shows stability of ghrelin in a blood sample collected from a fasting human subject over time, and collected and stored in both spiked (◆) and unspiked (■) EDTA-tubes and collection tubes containing a representative stabilization agent (including MAFP as the LysoPLA inhibitor) of the present invention (both spiked (▲) and unspiked (x)).

In a separate experiment, blood was drawn from a fasting subject in EDTA and EDTA+MAFP. The final MAFP tube concentration in this experiment was 0.1 mM. The plasma was separated from each tube into two separate vials. One vial was spiked with 1 pg/uL of ghrelin while the other was not spiked. Plasma spiked and upspiked from both EDTA and EDTA+MAFP were incubated at room temperature over 30 hours. FIG. 3 displays the measured ghrelin levels at specific time intervals. The data clearly demonstrate greater acyl-ghrelin stability in the tubes containing MAFP.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A collection device for collecting whole blood or a fluid component thereof, comprising a first end and a second end and at least one interior wall defining a reservoir, wherein the reservoir comprises a stabilization agent comprising a lysophospholipase (LysoPLA) inhibitor which stabilizes acylated proteins and acylated peptides that may be present in the collected whole blood or fluid component thereof, wherein the device further comprises an anti-coagulant, and wherein the device is a tube that is at least partially evacuated and which further comprises a closure pierceable by a needle for supplying blood to the reservoir.

2. The device of claim 1, wherein the tube is sterile.

3. The device of claim 1, wherein the interior wall comprises plastic or glass.

4. The device of claim 1, wherein the reservoir comprises a separating element.

5. The device of claim 1, wherein the LysoPLA inhibitor is methyl arachidonyl fluorophosphonate (MAFP).

6. The device of claim 1, wherein the LysoPLA inhibitor is selected from the group consisting of bromoenol lactone, ethyl octylphosphonofluoridate, isopropyl dodecylphosphonofluoridate, n-dodecyl-benzodioxaphosphorine 2-oxide, bromoenol lactone, palmityl trifluoromethyl ketone and palmitoyl carnitine.

7. The device of claim 1, wherein the stabilization agent further comprises a butylcholinesterase (BChE) inhibitor, an acetylcholinesterase (AChE) inhibitor, or a combination thereof.

8. The device of claim 7, wherein the BChE inhibitor is tacrine, or a derivative thereof.

9. The device of claim 1, wherein the stabilization agent further comprises a protease inhibitor.

10. The device of claim 9, wherein the protease inhibitor is an inhibitor of a serine protease, an inhibitor of an endoprotease, an inhibitor of an exopeptidase, an inhibitor of a dipeptidyl peptidase, or a combination of two or more thereof.

11. The device of claim 1, wherein the stabilization agent is Lyophilized.

12. The device of claim 1, wherein the anti-coagulant is EDTA or a salt thereof, or heparin.

13. The device of claim 12, wherein the anti-coagulant is coated or spray-dried onto at least a portion of the interior wall.

14. The device of claim 1, wherein the stabilization agent excludes an esterase inhibitor.

15. A method for collecting whole blood or a fluid component thereof, comprising collecting whole blood or the fluid component thereof from a patient into the device of claim 1.

16. The method of claim 15, wherein the whole blood or fluid component thereof is obtained from a diabetes patient.

17. The method of claim 15, wherein the fluid component is plasma.

18. A method for diagnosing a metabolic disease or monitoring treatment of a patient with a metabolic disease, comprising measuring at at least one predetermined time the presence or amount of ghrelin in a sample of whole blood or fluid component thereof, wherein the blood was collected from the patient into a collection device for collecting whole blood or a fluid component thereof, comprising a first end and a second end and at least one interior wall defining a reservoir, wherein the reservoir comprises a stabilization agent comprising a lysophospholipase (LysoPLA) inhibitor which stabilizes acylated proteins and acylated peptides that may be present in the collected whole blood or fluid component thereof, wherein a measured amount higher than a control is indicative of the presence of a metabolic disease, or efficacy of therapy.

19. A method for detecting the presence or amount of a prodrug and/or an active metabolite thereof in whole blood or a fluid component thereof, comprising detecting the presence or measuring the amount of a prodrug that bears an aliphatic ester group in a sample of blood or fluid component thereof, from a patient who has been administered the prodrug, wherein the blood or fluid component thereof was collected into a collection device of for collecting whole blood or fluid component thereof, comprising a first end and a second end and at least one interior wall defining a reservoir, wherein the reservoir comprises a stabilization agent comprising a lysophospholipase (LysoPLA) inhibitor which stabilizes acylated proteins and acylated peptides that may be present in the collected whole blood or fluid component thereof, and comparing the detected presence or measured amount to a control.

20. A collection device for collecting whole blood or a fluid component thereof, comprising a first end and a second end and at least one interior wall defining a reservoir, wherein the reservoir comprises a stabilization agent comprising a lysophospholipase (LysoPLA) inhibitor which stabilizes acylated proteins and acylated peptides that may be present in the collected whole blood or fluid component thereof, and a protease inhibitor, and wherein the device further comprises two or more protease inhibitors.

21. A collection device for collecting whole blood, or a fluid component thereof, comprising a first end and a second end and at least one interior wall defining a reservoir, wherein the reservoir comprises a stabilization agent comprising a lysophospholipase (LysoPLA) inhibitor which stabilizes acylated proteins and acylated peptides that may be present in the collected whole blood or a fluid component thereof, and a butylcholinesterase (BChE) inhibitor, an acetylcholinesterase (AChE) inhibitor, or a combination thereof.

22. A method for collecting whole blood , comprising collecting whole blood or a fluid component thereof from a diabetes patient into a device for collecting whole blood, comprising a first end and a second end and at least one interior wall defining a reservoir, wherein the reservoir comprises a stabilization agent comprising a lysophospholipase (LysoPLA) which stabilizes acylated proteins and acylated peptides that may be present in the collected whole blood or fluid component thereof.

23. A method for collecting whole blood or plasma, comprising collecting blood or plasma from a patient into a device for collecting whole blood or plasma, comprising a first end and a second end and at least one interior wall defining a reservoir, wherein the reservoir comprises a stabilization agent comprising a lysophospholipase (LysoPLA) which stabilizes acylated proteins and acylated peptides that may be present in the collected whole blood or plasma.

24. The device of claim 20, which is a tube that is at least partially evacuated and which further comprises a closure pierceable by a needle for supplying blood to the reservoir.

25. The device of claim 21, which is a tube that is at least partially evacuated and which further comprises a closure pierceable by a needle for supplying blood to the reservoir.

26. The device of claim 20, further comprising an anticoagulant.

27. The device of claim 21, further comprising an anticoagulant.

28. A method for collecting whole blood or a fluid component thereof, comprising collecting whole blood or fluid component thereof from a patient into the device of claim 9.

29. The method of claim 28, wherein the patient is a diabetic and the acylated proteins and acylated peptides that may be present in the collected whole blood or fluid component thereof comprise glucagon, $GIP_{(1-42)}$, GLP-1-(7-36)$NH_2$, GLP-1-(7-37), or a combination of two or more thereof.

30. The method of claim 18, which is a tube that is at least partially evacuated and which further comprises a closure pierceable by a needle for supplying blood to the reservoir.

31. The method of claim 19, which is a tube that is at least partially evacuated and which further comprises a closure pierceable by a needle for supplying blood to the reservoir.

32. The method of claim 22, which is a tube that is at least partially evacuated and which further comprises a closure pierceable by a needle for supplying blood to the reservoir.

33. The method of claim 23, which is a tube that is at least partially evacuated and which further comprises a closure pierceable by a needle for supplying blood to the reservoir.

34. The device of claim 20, wherein the LysoPLA inhibitor is methyl arachidonyl fluorophosphonate (MAFP).

35. The device of claim 21, wherein the LysoPLA inhibitor is methyl arachidonyl fluorophosphonate (MAFP).

* * * * *